(12) United States Patent
Oyaski

(10) Patent No.: US 7,331,770 B2
(45) Date of Patent: Feb. 19, 2008

(54) DISPOSABLE TWO-STAGE PUMP

(76) Inventor: Michael F. Oyaski, 207 E. Highland Ave., Edensburg, PA (US) 15931

( * ) Notice: Subject to any disclaimer, the term of this patent is extended or adjusted under 35 U.S.C. 154(b) by 518 days.

(21) Appl. No.: 10/341,724

(22) Filed: Jan. 14, 2003

(65) Prior Publication Data
US 2004/0138617 A1 Jul. 15, 2004

(51) Int. Cl.
*F04B 23/14* (2006.01)
(52) U.S. Cl. ........................ 417/201; 417/420
(58) Field of Classification Search ............ 417/199.1, 417/201, 223, 319, 420
See application file for complete search history.

(56) References Cited
U.S. PATENT DOCUMENTS

| 2,625,106 | A | * | 1/1953 | Hoffman | 417/201 |
| 2,655,110 | A | * | 10/1953 | Sanborn | 417/199.1 |
| 4,606,698 | A | | 8/1986 | Clausen et al. | |
| 4,621,982 | A | * | 11/1986 | Schulz et al. | 417/201 |
| 4,898,518 | A | | 2/1990 | Hubbard et al. | |
| 5,183,392 | A | * | 2/1993 | Hansen | 417/205 |
| 5,195,960 | A | | 3/1993 | Hossain et al. | |
| 5,466,131 | A | * | 11/1995 | Altham et al. | 417/420 |
| 6,494,686 | B1 | * | 12/2002 | Ward | 417/199.1 |
| 6,585,493 | B2 | * | 7/2003 | Sutton | 417/199.2 |

FOREIGN PATENT DOCUMENTS

JP 2-181091 * 7/1990

* cited by examiner

*Primary Examiner*—Michael Koczo, Jr.
(74) *Attorney, Agent, or Firm*—James Ray & Assoc.

(57) ABSTRACT

A disposable device for transfer of at least one predetermined medium into a device for treatment and promotion of healing of damaged body tissue. The device is comprised of a housing and a first pump stage disposed within the housing for pumping a first predetermined medium. A second pump stage engageable with such housing is included for pumping a second predetermined medium. Also included is a drive mechanism for driving the first and second pump stages. A coupling device engageable with the drive mechanism for connecting the drive mechanism to a power source is further included.

14 Claims, 2 Drawing Sheets

DISPOSABLE TWO-STAGE PUMP

CROSS-REFERENCE TO RELATED APPLICATIONS

This application is closely related to my co-pending U.S. patent application Ser. No. 09/874,539 filed Jun. 5, 2001, titled "Device for Treating and Healing Damaged Body Tissue". The teachings of this co-pending application are incorporated herein by reference thereto.

FIELD OF THE INVENTION

The present invention generally relates to a pump for pumping fluids. More particularly, the invention relates to a disposable, sterile, inexpensive pump with one or two interconnected stages capable of pumping one or more fluids simultaneously, and is separable from its associated power and control sources.

BACKGROUND OF THE INVENTION

There are many types of devices available to transfer medical fluids from a container to the patient. There are peristaltic pumps, rotary pumps, and cassette pumps. Among these devices are pumps having disposable sections, and/or are made from a sterile material. U.S. Pat. No. 4,898,518 (Hubbard et al.), discusses a shaft driven disposable centrifugal pump designed for pumping blood. U.S. Pat. No. 4,606,698 (Clausen et al.), discusses a shaft driven centrifugal pump designed for pumping blood.

There are also many types of devices available for the purpose of keeping an item inflated to a certain level. They range from the fans that keep large scale devices inflated (balloons, "moon jump" toys, etc.) to those that inflate smaller items such as inner tubes and pool float toys. In the medical industry, pumps are used for infusion of air into a patients lungs, and for orthopedic bracing.

U.S. Pat. No. 5,195,960 (Hossain et al.) discusses a dual peristaltic pumping/diaphragm vacuum diaphragm head for infusing/aspiration procedures. The teachings of the '960 patent include a disposable cassette, and a device that is made from a sterile material.

However, research has not uncovered a device that will suffice for the intentions of the preferred embodiment of the device disclosed in this patent.

SUMMARY OF THE INVENTION

In one aspect, the invention provides a disposable device for the transfer of at least one predetermined medium into a device for the treatment and promotion of healing of damaged body tissue. The device includes a housing, and a first pump means disposed within the housing for pumping a first predetermined medium. The device further includes a second pump means engageable with the housing for pumping a second predetermined medium. Also included is a drive means for the first and second pump means. Finally, a coupling means engageable with the drive means is included for connecting the drive means to a power source.

OBJECTS OF THE INVENTION

It is an object of the present invention to provide a disposable pumping device that is able to transfer one or more fluids simultaneously.

It is another object of the present invention to provide a disposable pumping device that is separable from an associated drive motor and control.

It is a further object of the present invention to provide a disposable pump that can transfer one or more fluids simultaneously and is made from a sterile material.

It is still another object of the present invention to provide a disposable pump that can transfer one or more fluids simultaneously, while minimizing cost.

In addition to the above-described objects and advantages of the disposable two-stage pump, various other objects and advantages of the present invention will become more readily apparent to the persons who are skilled in the same and related arts from the following more detailed description of the invention, particularly, when such description is taken in conjunction with the attached drawing figures and the appended claims.

DETAILED DESCRIPTION OF THE PREFERRED EMBODIMENT

Figure 1A:
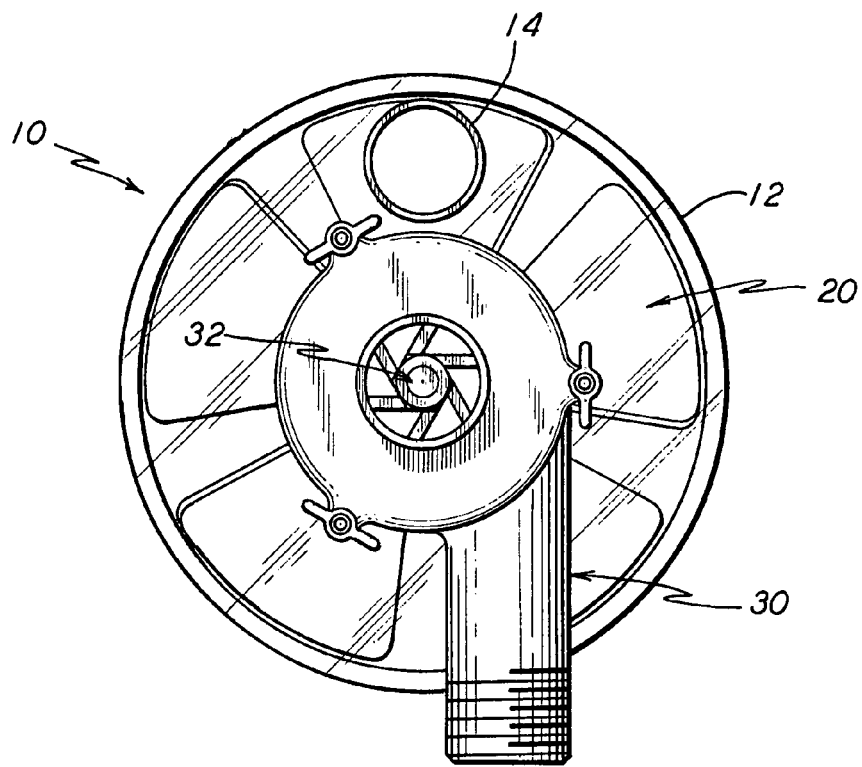
FIG. 1A provides a top view of a disposable pump according to a presently preferred embodiment of the invention.

Prior to proceeding to a much more detailed description of the present invention, it should be noted that identical components which have identical functions have been identified with identical reference numerals throughout the several views illustrated in the drawing figures for the sake of clarity and understanding of the invention.

Figure 1B:
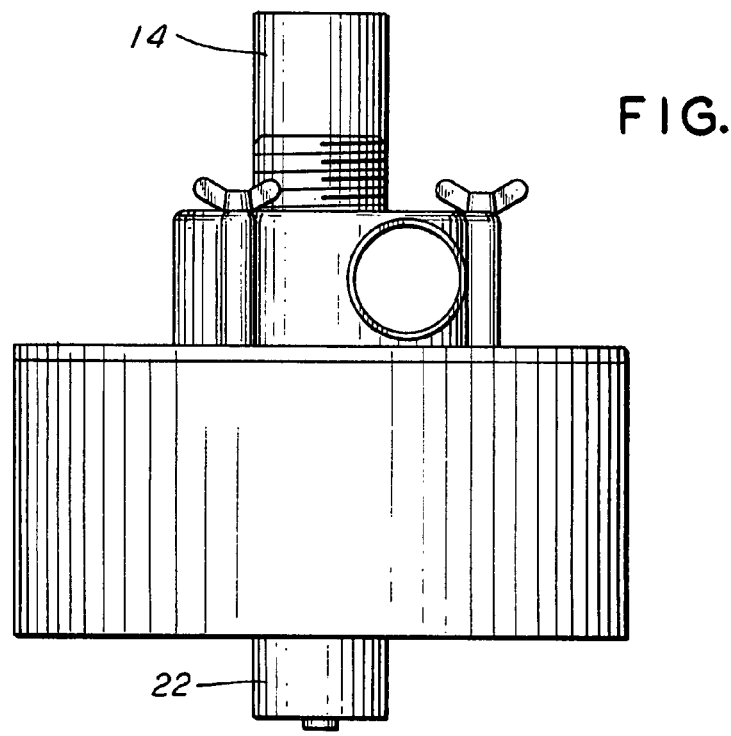
FIG. 1B provides a side view of a disposable pump according to a presently preferred embodiment of the invention.
Figure 2:
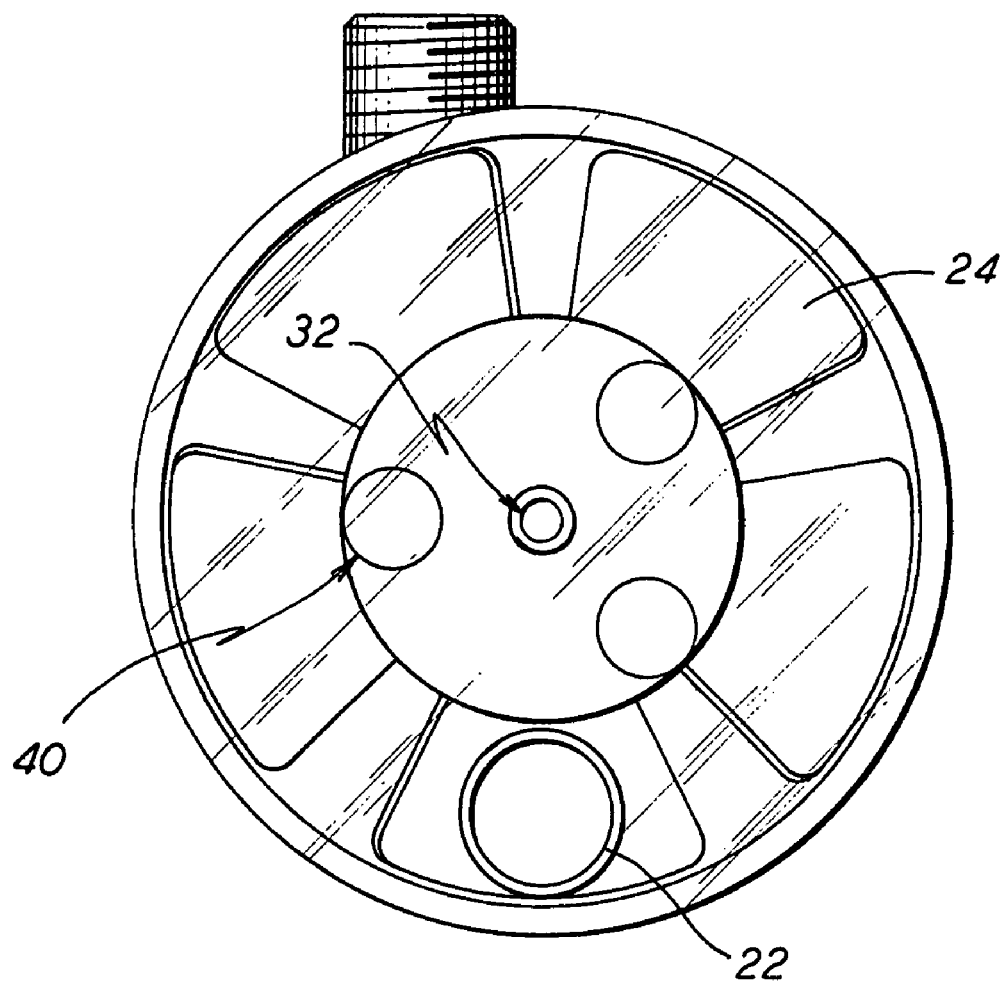
FIG. 2 is a back view of the disposable pump illustrated in FIGS. 1A and 1B.

Referring initially to FIGS. 1 and 2 a disposable two-stage pump constructed according to the present invention is generally indicated by reference numeral 10. The disposable two-stage pump (10) includes a housing 12 made from a clear material to enable observation of a predetermined medium pumped by a first pump means 20.

The first pump means 20 is disposed within the housing 12, and is for pumping a first predetermined medium to a device for the treatment and promotion of healing of damaged body tissue (not shown). The first pump means 20 can be one of an axial flow, centrifugal, gear, peristaltic, radial flow, rotary vane, and screw type pump. In the presently preferred embodiment, the first pump means 20 for pumping a gaseous fluid is an axial flow type pump, wherein at least an outer end of the impeller blades 24 of such axial flow pump are metallic. The first pump means 20 further includes an inlet 22 and an outlet 14 of a predetermined inner diameter and have centerlines substantially in alignment with each other.

A second pump means 30 is disposed within the housing 12 for pumping a second predetermined medium to a device for the treatment and promotion of healing of damaged body tissue. The second pump means 30 can be one of an axial flow, centrifugal, gear, peristaltic, radial flow, rotary vane, and screw type pump. In the presently preferred embodiment, the second pump means 30 is a centrifugal type pump.

A drive means 32 for the first and second pump means is included. In the presently preferred embodiment, the first pump means and second pump means have a common drive 32 disposed on a common centerline. The drive means 32 turns the impellers of the first pump means 20 and second pump means 30, and is engageable with a coupling means 40.

The coupling means 40 engageable with such drive means 32 is included for connecting and disconnecting such drive means 32 with a power source (not shown). The power source is at least one of an electric motor and a pneumatic fluid. The coupling means 40 is preferably magnetic, and contained within the housing 10 of the first pump means 20 in the presently preferred embodiment. It is an option to have the coupling means 40 located external to the housing 10 of the first pump means 20 and such second pump means 30. In either external or internal applications of the drive means 32, it is sealed against fluid leakage.

The invention further includes a magnetic engaging means (not shown) for engaging such coupling means 40 and a control means (not shown) for controlling operation of the power source. The control means provides positive engagement of the engaging means and the coupling means 40 during start up.

While the present invention has been described by way of a detailed description of a particularly preferred embodiment, it will be readily apparent to those of ordinary skill in the art that various substitutions of equivalents may be affected without departing from the spirit or scope of the invention set forth in the appended claims.

I claim:

1. In combination with a device for treatment and promotion of healing of damaged body tissue, the improvement comprising a disposable pump having:
   (a) a housing;
   (b) a first axial flow type pump means disposed within said housing for pumping a first predetermined medium;
   (b) a second pump means engageable with said housing for pumping a second predetermined medium;
   (d) a drive means for said first and said second pump means; and
   (e) a magnetic coupling means contained within said housing of said first pump means and is engageable with said drive means for connecting said drive means to a power source.

2. The combination according to claim 1, wherein said second pump means is one of an axial flow, centrifugal, gear, peristaltic, radial flow, rotary vane, and screw type pump.

3. The combination according to claim 1, wherein said first pump means and said second pump means have a common drive.

4. The combination according to claim 2, wherein said second pump means is a centrifugal type pump.

5. The combination according to claim 1, wherein said first pump means further includes an inlet and an outlet of a predetermined inner diameter and have an outer diameter substantially adjacent an inner diameter of said pump housing and have centerlines substantially in alignment with each other and are oriented axially to said common drive means and are located on opposing faces of said first pump housing.

6. The combination according to claim 1, wherein at least an outer end of impeller blades of said axial flow pump are metallic.

7. The combination according to claim 3, wherein said common drive means is sealed against fluid leakage.

8. The combination according to claim 1, wherein said power source further includes a engaging means for engaging said coupling means and a control means for controlling operation of said power source.

9. The combination according to claim 8, wherein said engaging means is magnetic.

10. The combination according to claim 8, wherein said control means provides positive engagement of said engaging means and said coupling means during start up.

11. The combination according to claim 8, wherein said power source is an electric motor.

12. The combination according to claim 1, wherein said power source is a fluid.

13. The combination according to claim 12, wherein said power source is pneumatic.

14. The combination according to claim 1, wherein said housing is made from a clear material to enable observation of said predetermined medium.

* * * * *